US009168276B2

(12) United States Patent
Bombardelli et al.

(10) Patent No.: US 9,168,276 B2
(45) Date of Patent: Oct. 27, 2015

(54) FORMULATIONS FOR THE TREATMENT OF DISORDERS OF THE UPPER RESPIRATORY TRACT

(75) Inventors: Ezio Bombardelli, Groppello Cairoli (IT); Massimo Ronchi, Milan (IT); Paolo Morazzoni, Milan (IT)

(73) Assignee: INDENA S.P.A., Milan (IT)

( * ) Notice: Subject to any disclaimer, the term of this patent is extended or adjusted under 35 U.S.C. 154(b) by 48 days.

(21) Appl. No.: 13/878,520

(22) PCT Filed: Oct. 5, 2011

(86) PCT No.: PCT/EP2011/067357
§ 371 (c)(1),
(2), (4) Date: Apr. 11, 2013

(87) PCT Pub. No.: WO2012/049045
PCT Pub. Date: Apr. 19, 2012

(65) Prior Publication Data
US 2013/0280355 A1    Oct. 24, 2013

(30) Foreign Application Priority Data

Oct. 11, 2010    (IT) .......................... MI2010A001852

(51) Int. Cl.
*A61K 36/45* (2006.01)
*A61K 36/28* (2006.01)
*A61K 36/185* (2006.01)
*A61K 36/00* (2006.01)

(52) U.S. Cl.
CPC .............. *A61K 36/00* (2013.01); *A61K 36/185* (2013.01); *A61K 36/28* (2013.01); *A61K 36/45* (2013.01)

(58) Field of Classification Search
None
See application file for complete search history.

(56) References Cited

U.S. PATENT DOCUMENTS

| 6,503,541 B1 * | 1/2003 | Moon et al. .................. 424/725 |
| 2007/0104661 A1 | 5/2007 | Bombardelli et al. |
| 2007/0275104 A1 * | 11/2007 | Kornman et al. ............. 424/729 |
| 2008/0057143 A1 | 3/2008 | Madjid |
| 2008/0145319 A1 | 6/2008 | Bombardelli et al. |
| 2009/0035226 A1 * | 2/2009 | Tempesta et al. ............... 424/48 |
| 2009/0297641 A1 * | 12/2009 | Levine et al. ................. 424/730 |
| 2011/0091392 A1 | 4/2011 | Bombardelli et al. |
| 2011/0335769 | 6/2011 | Bombardelli et al. |

OTHER PUBLICATIONS

James B. Hudson, The Use of Herbal Extracts in the Control of Influenza, Journal of Medicinal Plants Research, vol. 3, pp. 1189-1195, 2009.
International Preliminary Report issued in counterpart International PCT Application No. PCT/EP2011/067357.
International Search Report issued in counterpart International PCT Application No. PCT/EP2011/067357.

* cited by examiner

*Primary Examiner* — Chris R Tate
*Assistant Examiner* — Randall Winston
(74) *Attorney, Agent, or Firm* — Silvia Salvadori, P.C.

(57) ABSTRACT

The present invention relates to formulations containing extracts of *Vaccinium myrtillus* or other species rich in anthocyanosides, *Punica granatum*, *Echinacea*, and optionally *Krameria triandra*. Said formulations are useful in the treatment of disorders of the mouth and its adnexa, the throat and respiratory tract, and in the treatment of influenza.

4 Claims, No Drawings

FORMULATIONS FOR THE TREATMENT OF DISORDERS OF THE UPPER RESPIRATORY TRACT

This application is a U.S. national stage of PCT/EP2011/067357 filed on Oct. 5, 2011, which claims priority to and the benefit of Italian Application No. MI2010A001852, filed on Oct. 11, 2010, the contents of which are incorporated herein by reference.

The present invention related to formulations containing extracts of *Vaccinium myrtillus* or other species rich in anthocyanosides, *Punica granatum, Echinacea*, and optionally *Krameria triandra*. Said formulations are useful in the treatment and prevention of disorders of the mouth and its adnexa, the throat and respiratory tract, and in the treatment of influenza.

In particular, the combinations according to the present invention, incorporated in suitable carriers, are particularly useful in bacterial and viral disorders of infancy.

INTRODUCTION

Reddening, inflammation and bacterial and/or fungal infection of the throat, with plaque formation, are symptoms that accompany common influenza, colds and similar disorders. The common cold and influenza, which affect both children and adults up to three times a year on average, are mainly associated with viral infections, 40% of which are caused by rhinovirus, 10% by coronavirus and a smaller proportion by adenovirus and parainfluenza virus.

The preventive and curative treatment of influenza is an important goal, because this illness affects millions of people worldwide every year, with major repercussions in terms of public health, due to the frequent serious complications which debilitate patients, leading to a serious risk of death, and in financial terms, due to loss of working hours.

Influenza is particularly dangerous in the elderly, due to its complications or to existing respiratory disorders which are typical of these patients. The same problem arises in infants, where influenza leaves an aftermath of continual colds and relapses. For many years, preventive vaccination was considered to be the most effective method of dealing with viral diseases; however, its efficacy is limited by an unusual antigen mutability due to the appearance of new variants of viruses able to overcome the immunity that withstood the earlier strains.

Although there is no specific treatment for these disorders, antihistamines, decongestants and anti-inflammatories are considered useful, because reduction of oedema alleviates pain and shortens the length of the disorder underlying the inflammation. These disorders sometimes involve complications due to the onset of secondary bacterial infections, because the outlets of the nasal sinuses are often obstructed by congestion of the mucous membranes where pathogenic germs can easily proliferate, causing fever and localised pain. In this case, antibiotic or bacteriostatic treatment is required in addition to symptomatic treatments. However, antibiotics lower the body's defences, especially in infants, leading to relapses.

The neuraminidase inhibitors introduced in the last decade also present low efficacy, and often problems of toxicity and inducement of resistance to viruses. These substances have different impacts on strains A and B, so substances which attack both strains are essential when the type of infection is not known a priori.

However, not all the preparations currently available on the market can be used by children and pregnant women. This means that antiviral preparations which are fairly harmless to both adult patients (including pregnant women) and children, and do not cause the development of resistant viruses, are essential.

DESCRIPTION OF THE INVENTION

It has now been discovered that formulations containing extract of *Vaccinium myrtillus* or of other species rich in anthocyanosides, *Punica granatum* extract, *Echinacea* extract, and optionally *Krameria triandra* extract, possess marked antiviral activity towards various strains of influenza A and B and towards adenovirus, paramyxovirus, herpes catarrhalis virus, cytomegalovirus and respiratory syncytial virus, together with considerable antimicrobial activity, and have consequently proved effective in the treatment of the disorders of the mouth and its adnexa, the throat and respiratory tract, and in the prevention and treatment of influenza.

The present invention therefore relates to new formulations containing:
 a) extract of *Vaccinium myrtillus* or other species rich in anthocyanosides;
 b) *Punica granatum* extract;
 c) *Echinacea* extract; and optionally
 d) *Krameria triandra* extract.

According to the present invention, the term "*Vaccinium myrtillus* or other species" comprises plants containing anthocyanosides. The anthocyanosides present in these plants are mainly cyanidin and delphinidin glucosides, for which activities relating to capillary protection, inflammation, angiogenesis and immunomodulation have been described.

The anti-inflammatory effect performed by anthocyanosides is associated with NFkB inhibition and with their anti-angiogenetic power; as the angiogenesis process is essential in inflammation and angiogenesis is dependent on VEGF (vascular endothelial growth factor), these parameters were evaluated, and activity was found at nanomolar level. Said molecules also inhibit 5- and 12-lipoxygenase at nanomolar concentration. Nuclear factor NF-kB, which is involved in both inflammation and the immune response to infections, is significantly inhibited by anthocyans and by tannins and metabolites thereof, and this factor is also inhibited at nanomolar concentrations.

According to the invention, *Punica granatum* extract is an extract obtained from fruit with a 90% polyphenol content. Said extract has demonstrated antiviral and mildly antibacterial properties, increasing the body's defences by greater synthesis of interferon γ.

The preparation of this extract comprises extraction from the fruit and/or aerial parts of the plants with C1-C3 alcohols variously diluted with water, preferably with a 50% v/v mixture of ethanol/water; subsequent concentration of the water/ethanol extract until the organic solvent has been completely eliminated, treatment of the cloudy suspension with a quantity of polyvinylpyrrolidone amounting to 0.2% of the weight of the biomass and filtration to eliminate the undesirable polymeric tannins, absorption of the clear solution on polystyrene resin and washing of the resin until the soluble substances have been completely eliminated. The active ingredient that constitutes the extract used in the present invention is recovered by washing the resin with 90% ethanol. Concentration of the ethanol eluate to a small volume and drying of the residue under vacuum at a temperature not exceeding 50° C. provides the polyphenol-enriched extract.

According to the invention, the *Echinacea* extract is preferably an alcoholic extract of the roots and aerial parts of *Echinacea angustifolia* and/or *purpurea*.

Antimicrobial and antiviral activity has been described for *Echinacea* extract, especially on strains of *Streptococcus pyogenes, Staphylococcus aureus* (penicillin-resistant), *Haemophilus influenzae* and *Legionella pneumophila*. These activities are associated with both the polyphenol part and the lipophilic part which is rich in isobutylamides of polyunsaturated acids (Phytomedicine, 17, 563, 2010). Isobutylamides are potent ligands of the cannabinoid and vanilloid TRPV1 receptors, and consequently act on pain, inflammation and the immune response. Cannabinoid agonist compounds are also associated with reinforcement of the immune response, as recently demonstrated for *Cannabis* derivatives.

According to the invention, *Krameria triandra* extract is a water/alcohol extract obtained from the roots and aerial parts of the plant, purified according to the procedure previously described for the preparation of *Punica granatum* extract. The *Krameria triandra* extract thus obtained has a 14% benzofuran content and a 70% ellagitannin and protocatechuic tannin content. *Krameria* extract is known for its antibacterial and antifungal action at concentrations of micrograms per mL.

It has now surprisingly been found that the formulations according to the invention possess antimicrobial and antiviral activity considerably exceeding those of the various extracts when administered separately, suggesting the presence of an in vivo synergic mechanism not foreseeable a priori in therapeutic or preventive terms, which in particular boosts the antimicrobial and antiviral activity of the substance.

The formulations according to the invention have proved highly active against the most common strains of viruses, especially the influenza virus, preventing the formation of bacterial plaques with fever which normally accompany colds and influenza. These formulations are also effective in purulent otitis and mouth infections in general.

According to a preferred aspect, the formulations according to the invention contain the active ingredients within the following weight intervals per unit dose:

a) extract of *Vaccinium myrtillus* or other species rich in anthocyanosides; 20 to 80 mg;

b) *Punica granatum* extract: 20 to 40 mg;

c) *Echinacea* extract: 20 to 100 mg; and optionally d) *Krameria triandra* extract: 10 to 30 mg.

According to a particularly preferred aspect, the compositions according to the invention will contain the following active ingredients in the following weight ranges per unit dose:

a) extract of *Vaccinium myrtillus* or other species rich in anthocyanosides; 40 to 60 mg;

b) *Punica granatum* extract: 25 to 35 mg;

c) *Echinacea* extract: 40 to 60 mg; and optionally d) *Krameria triandra* extract: 15 to 20 mg.

The pharmaceutical formulations to be used are mainly formulated as tablets which dissolve slowly in the oral cavity, or as chewing gums which allow slow release of the active constituents. These formulations are mainly used in preventive treatments, but also curatively, and for oral hygiene.

Said formulations will therefore be prepared according to well-known conventional methods, such as those described in "Remington's Pharmaceutical Handbook", Mack Publishing Co., N.Y., USA, together with suitable excipients.

The following examples illustrate the invention in detail.

EXAMPLE I

1000 mg Chewable Tablets Containing

| | |
|---|---|
| *Punica granatum* extract | 30.0 mg |
| *Vaccinium myrtillus* extract (40% anthocyanosides) | 60.0 mg |
| *Echinacea* extract | 50.0 mg |
| Mannitol | 429.5 mg |
| Fructose | 300.0 mg |
| Anhydrous citric acid | 10.0 mg |
| Carboxymethylcellulose sodium salt | 40.0 mg |
| Glyceryl behenate | 20.0 mg |
| Sodium saccharine | 0.5 mg |
| Soft fruit flavouring | 20.0 mg |

EXAMPLE II

1000 mg Chewable Tablets Containing

| | |
|---|---|
| *Punica granatum* extract | 40.0 mg |
| *Vaccinium myrtillus* extract (40% anthocyanosides) | 80.0 mg |
| *Krameria triandra* extract | 35.0 mg |
| *Echinacea* extract | 50.0 mg |
| Saccharose | 472.0 mg |
| Mannitol | 230.0 mg |
| Anhydrous citric acid | 10.0 mg |
| Carboxymethylcellulose sodium salt | 40.0 mg |
| Glyceryl behenate | 20.0 mg |
| Sodium saccharine | 0.5 mg |
| Ammonium glycyrrhizinate | 3.0 mg |
| Soft fruit flavouring | 20.0 mg |

EXAMPLE III

Granulate for Extempore Suspension Containing

| | |
|---|---|
| *Punica granatum* extract | 40.0 mg |
| *Vaccinium myrtillus* extract (40% anthocyanosides) | 60.0 mg |
| *Krameria triandra* extract | 20.0 mg |
| *Echinacea* extract | 50.0 mg |
| Mannitol | 900.0 mg |
| Guar gum | 100.0 mg |
| Sodium cyclamate | 21.0 mg |
| Anhydrous citric acid | 30.0 mg |
| Ammonium glycyrrhizinate | 10.0 mg |
| Acesulfame K | 3.0 mg |
| Hydroxypropylcellulose | 1.0 mg |

EXAMPLE IV

Granulate for Extempore Suspension Containing

| | |
|---|---|
| *Punica granatum* extract | 40.0 mg |
| *Vaccinium myrtillus* extract (40% anthocyanosides) | 60.0 mg |
| *Echinacea* extract | 50.0 mg |
| Mannitol | 920.0 mg |
| Guar gum | 100.0 mg |
| Sodium cyclamate | 21.0 mg |
| Anhydrous citric acid | 30.0 mg |
| Ammonium glycyrrhizinate | 10.0 mg |

| | |
|---|---|
| Acesulfame K | 3.0 mg |
| Hydroxypropylcellulose | 1.0 mg |

EXAMPLE V

Biological Activity

The compositions according to the invention were tested on six groups of 10 patients of both sexes suffering from bacterial infection of the oral cavity.

The patients were treated with tablets containing the combination (Example II) or the single ingredient, 3 times a day for 3 days. One hour before the first treatment and one hour after the last treatment, the hyperaemia of the pharynx and tonsils was also evaluated on a 4-point scale (none=0, slight=1, moderate=2, severe=3).

The results are set out in Table 1.

TABLE 1

| | Inflammation of pharynx and tonsils | |
|---|---|---|
| | Baseline value | Post-treatment |
| Tablet described in example II, only containing 30 mg of *Punica granatum* extract | 2.2 | 1.9 |
| Tablet described in example II, only containing 60 mg of *Vaccinium myrtillus* extract (40% anthocyanosides) | 1.9 | 1.5 |
| Tablet described in example II, only containing 50 mg of *Echinacea* extract | 1.8 | 1.7 |
| Tablet described in example II, only containing 20 mg of *Krameria triandra* extract | 2.1 | 2.0 |
| Tablet described in example II | 2.3 | 0.4 |
| Placebo | 1.8 | 1.8 |

At the same time, the patients gargled for 20 s with 10 mL of sterile distilled water, and samples were collected.

The samples were suitably diluted in Ringer solution containing 0.2% dithiothreitol, and 0.5 ml of each dilution was plated on 4 agar plates (Columbia) supplemented with 5% of sheep blood; the plates were incubated in $CO_2$ atmosphere for 72 hours for the anaerobic culture. After incubation, the number of colonies was counted.

The results are set out in Table 2.

TABLE 2

| | Bacteria count ($\times 10^5$) in samples obtained from gargling | |
|---|---|---|
| | Baseline value | Post-treatment |
| Tablet described in example II, only containing 30 mg of *Punica granatum* extract | 37.0 | 33.0 |
| Tablet described in example II, only containing 60 mg of *Vaccinium myrtillus* extract (40% anthocyanosides) | 38.4 | 30.4 |
| Tablet described in example II, only containing 50 mg of *Echinacea* extract | 29.9 | 27.3 |
| Tablet described in example II, only containing 20 mg of *Krameria triandra* extract | 31.4 | 26.3 |
| Tablet described in example II | 36.2 | 6.7 |
| Placebo | 31.1 | 30.9 |

The invention claimed is:

1. A dosage formulation for treating disorders of the mouth, throat and respiratory system and/or for treating influenza comprising the following weight ranges per unit dose:
   a) a *Vaccinium myrtillus* extract, in an amount from 20 to 80 mg;
   b) a *Punica granatum* extract, in an amount from 20 to 40 mg;
   c) an *Echinacea* extract, in an amount from 20 to 100 mg; and optionally
   d) a *Krameria trianda* extract, in an amount from 10 to 30 mg.

2. The dosage formulation as claimed in claim 1, wherein the *Punica granatum* extract is an extract obtained from fruit having a 90% polyphenol content.

3. The dosage formulation as claimed in claim 1, wherein the *Krameria triandra* extract is a water/alcohol extract obtained from the roots and aerial parts of the plant having a 14% benzofuran content and a 70% ellagitannin and protocatechuic tannin content.

4. The dosage formulation as claimed in claim 1, comprising the following weight ranges per unit dose:
   a) the *Vaccinium myrtillus* extract, in an amount from 40 to 60 mg;
   b) the *Punica granatum* extract, in an amount from 25 to 35 mg;
   c) the *Echinacea* extract, in an amount from 40 to 60 mg; and optionally
   d) the *Krameria trianda* extract, in an amount from 15 to 20 mg.

\* \* \* \* \*